(12) United States Patent
Melrose et al.

(10) Patent No.: US 7,629,002 B2
(45) Date of Patent: Dec. 8, 2009

(54) ANTIMICROBIAL POLYMERIC COMPOSITIONS AND METHOD OF TREATMENT USING THEM

(75) Inventors: Graham John Hamilton Melrose, Dalkeith (AU); Andrew James Huxham, Balga (AU)

(73) Assignee: Chemeq Ltd., Bentley (AU)

( * ) Notice: Subject to any disclaimer, the term of this patent is extended or adjusted under 35 U.S.C. 154(b) by 435 days.

(21) Appl. No.: 10/053,088

(22) Filed: Jan. 18, 2002

(65) Prior Publication Data

US 2003/0195131 A1    Oct. 16, 2003

Related U.S. Application Data

(63) Continuation-in-part of application No. 10/009,139, filed as application No. PCT/AU00/00107 on Feb. 16, 2000, now Pat. No. 6,803,356.

(51) Int. Cl.
*A01N 25/02*    (2006.01)

(52) U.S. Cl. .................. 424/438; 424/435; 424/436; 424/442; 424/457

(58) Field of Classification Search .............. 510/415; 424/400–404, 59, 78.02–78.08, 438, 484, 424/488, 435, 436, 442, 457; 514/336
See application file for complete search history.

(56) References Cited

U.S. PATENT DOCUMENTS

| 4,479,820 | A |   | 10/1984 | Merk et al. |   |
|---|---|---|---|---|---|
| 4,711,892 | A | * | 12/1987 | Manoury et al. | 514/336 |
| 4,724,142 | A |   | 2/1988 | Mahn et al. |   |
| 4,724,143 | A |   | 2/1988 | Mahn et al. |   |
| 4,847,392 | A | * | 7/1989 | Gassman et al. | 549/430 |
| 5,290,894 | A |   | 3/1994 | Melrose et al. |   |
| 5,917,094 | A |   | 6/1999 | Werle et al. |   |
| 6,060,571 | A |   | 5/2000 | Werle et al. |   |
| 6,410,040 | B1 | * | 6/2002 | Melrose et al. | 424/404 |
| 6,723,336 | B1 | * | 4/2004 | Melrose | 424/438 |
| 2002/0127207 | A1 | * | 9/2002 | Harris et al. | 424/93.6 |

FOREIGN PATENT DOCUMENTS

| AU | 11686/95 |   | 8/1995 |
|---|---|---|---|
| AU | 14844/97 |   | 8/1997 |
| GB | 1509154 |   | 4/1978 |
| WO | WO 96/38186 | * | 12/1996 |
| WO | 00/03723 | * | 1/2000 |
| WO | WO 00/03723 | * | 1/2000 |
| WO | WO 01/60874 | * | 8/2001 |

* cited by examiner

*Primary Examiner*—Lorna M Douyon
*Assistant Examiner*—Amina Khan
(74) *Attorney, Agent, or Firm*—Nixon Peabody LLP

(57) ABSTRACT

A polymeric antimicrobial comprising a derivative of poly(2-propenal, 2-propenoic acid) formed by reaction between a poly(2-propenal, 2-propenoic acid) and an alcohol or phenol to form protected carbonyl groups. The invention also relates to antiseptic compositions and compositions for treating gastrointestinal disease containing the polymeric antimicrobial.

28 Claims, No Drawings

ANTIMICROBIAL POLYMERIC COMPOSITIONS AND METHOD OF TREATMENT USING THEM

This application is a continuation-in-part of U.S. patent application Ser. No. 10/009,139, now U.S. Pat. 6,803,356, which is a national stage application of PCT/AU00/00107, filed Feb. 16, 2000.

FIELD OF THE INVENTION

The present invention relates to antimicrobial polymeric compositions to methods of preparing antimicrobial polymeric compositions and the use as growth promoters and in treatment or prophylaxis of gastrointestinal disease using them.

BACKGROUND ART

Acrolein polymers and their biocidal properties have been described by Melrose et al in international publication WO 88/04671. These polymers (referred to as the subject polymers) have a repeating unit of formula I

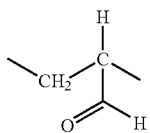

(I)

; or this unit in its hydrated, hemi-acetal or acetal form, represented by the formulae:

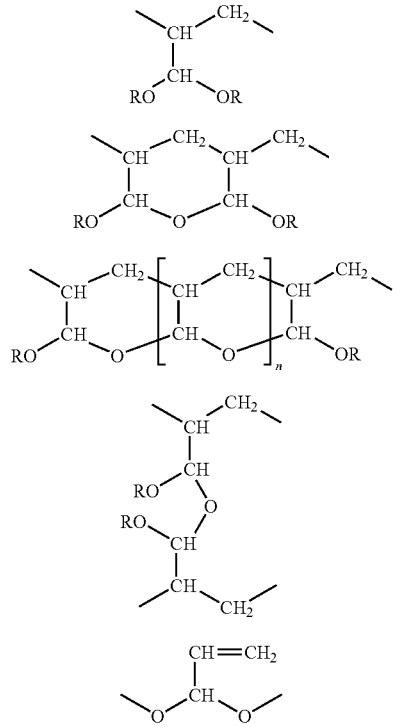

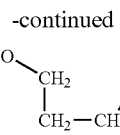

(f)

wherein R is hydrogen and n is an integer of one or more, have been demonstrated previously. German Patent Application P4404404 and equivalents such as EP667358 and AU 11686/95 (now lapsed) discloses a process in which acrolein is polymerized in an aqueous sodium hydroxide medium. The disclosure states that the resulting polyacrolein is soluble in polyhydric alcohol at 40 to 50° C. to form a solution of the polyacrolein in a polyhydric alcohol. As explained below the assignee of this German application subsequently found such polymers to be problematic and have low solubility in aqueous media.

International Patent Publication WO 96/38186 discloses a process for preparation of poly(2-propenal, 2-propenoic acid) wherein the aldehyde groups of poly(2-propenal) syn polyacrolein are partially auto-oxidised to carboxyl groups, by heating the dry polymer in air, to 100° C. and preferably to between 80° C. and 100° C. The poly(2-propenal, 2-propenoic acid) polymers typically contain 0.1 to 5 moles of carboxyl groups per kilogram. The resulting polymers have significantly improved solubility in dilute aqueous bases, for example aqueous sodium carbonate.

European publication No. 792895 Werle et al (corresponding to U.S. Pat. No. 6,060,571) relates to acrolein releasing polymers prepared by copolymerisation of acrolein monomer and a polyhydric alcohol. Werle et al observe that the polyacroleins described in German Application No. P4404404 are problematic in that the yield is less than desired and the polymers are virtually insoluble in water. European Application 792895 teaches that these problems are overcome by forming an acrolein releasing polymer by copolymerisation of acrolein monomer and a polyhydric alcohol monomer. The proposed structure of the copolymer is as follows:

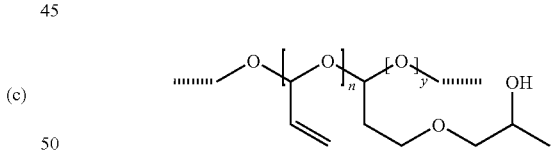

While free acrolein acts as an antimicrobial it is irritating to the eyes, lungs, tissues and skin. There is a need in a range of applications including on skin and in gastrointestinal treatments for antimicrobials which are stable, highly water soluble, and safe to use.

SUMMARY OF THE INVENTION

We have now found the activity and stability of poly(2-propenol, 2-propenoic acid) polymers are substantially increased if they are reacted with an alcohol or polyol to form protected carbonyl groups such as acetal and/or hemiacetal derivatives. Surprisingly we have found that the activity of the derivative is substantially increased notwithstanding that the free acrolein content may be extremely low or negligible in the polymer in water. The solubility of the polymer is also very high.

Accordingly, the invention provides an antimicrobial comprising a derivative of poly(2-propenal, 2-propenoic acid) formed by reaction between poly(2-propenal, 2-propenoic acid) and an organic compound containing hydroxyl group such as an alcohol or phenol, preferably selected from alkanols, phenols, polyols and mixtures thereof, to form protected carbonyl groups. A polyol is meant as a molecule at least two hydroxyl groups. The derivatives formed are typically selected from hemiacetal and acetal derivatives.

Without wishing to be bound by theory we believe that the reaction of the poly(2-propenal, 2-propenoic acid) with the alcohol forms hemiacetal and/or acetal groups from at least a proportion of the pendent aldehyde groups thereby stabilizing the carbonyl groups of the polymers against alkaline degredation by the Cannizarro reaction. The formation of acetal groups has been found to significantly reduce or eliminate the release of free acrolein while surprisingly increasing the activity of the resulting derivative.

In a further aspect the invention provides a method of treatment or prophylaxis of gastrointestinal disease in an animal (including humans) comprising administering to the animal an antimicrobially effective amount of the above described antimicrobial.

The invention further provides compositions of the antimicrobial for use as antiseptics, disinfectants and in treatment of gastrointestinal disease.

DETAILED DESCRIPTION OF THE INVENTION

The antimicrobial of the invention may be prepared by heating poly(2-propenal, 2-propenoic acid) in the presence of the alcohol, preferably a polyol such as polyethylene glycol. Water is invariably present in the alcohols and it will be understood that the presence of at least some water assists in the nucleophilic reaction resulting in hemiacetal or acetal formation.

The solution is generally heated at a temperature in the range of from 40° C. to 150° C., more preferably 40 to 115° C. and most preferably 70 to 115° C.

The antimicrobial of the invention is prepared from poly (2-propenal, 2-propenoic acid) polymers. Such polymers and their preparation are described in International Patent Publication No. WO 96/38186 (PCT/AU96/00328) the contents of which are herein incorporated by reference. The poly(2-propenal, 2-propenoic acid) polymers are preferably prepared by polymerization of acrolein preferably in aqueous solution by anionic polymerization, followed by autoxidation. The polymers contain the repeating unit of formula I and at least one (and typically a mixture) of the hydrated, hemiacetal and acetal forms.

The hydrated, hemiacetal and acetal forms formed by polymerization of acrolein are known to arise from the various carbon-carbon and carbon-oxygen polymerization mechanisms of acrolein. For example the hydrated form is typically the hydrated diol form, the hemiacetal or acetal form may be formed from the condensation of the diol form with the aldehyde or diol form, the tetrahydropyran or fused tretrahydropyran form may be formed from condensation of the diol form and the aldol-Michael self condensation form. Typical examples of these forms are shown in formula (a) to (f) below:

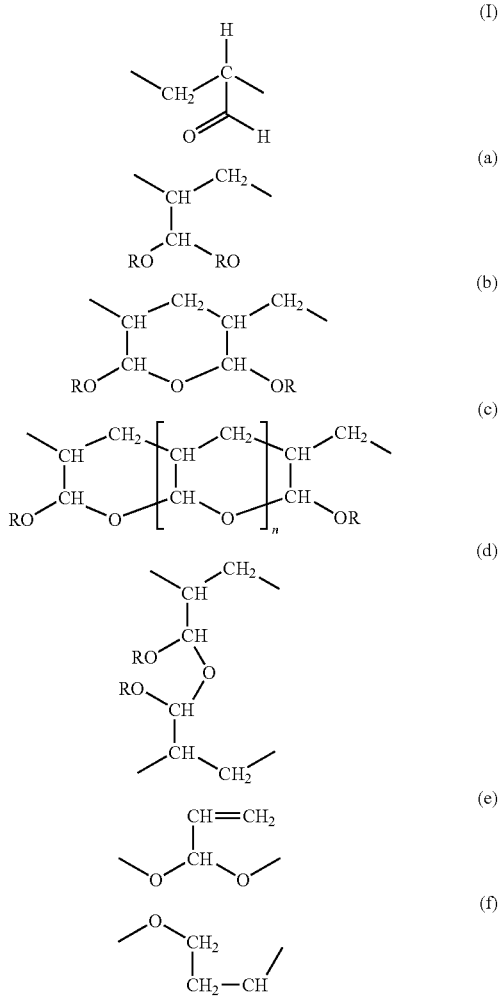

wherein R is hydrogen and n is an integer of one or more. The proportion of repeating unit of formula I is typically less than 20% and frequently from 5 to 15%. Notwithstanding the relatively low proportion of these units we have found that they have a significant effect on the stability of the polymer.

The poly(2-propenal, 2-propenoic acid) will generally contain no more than 10% on a molar basis of monomer units from monomers other than acrolein and is most preferably an acrolein homopolymer (before autoxidation). Where used other monomers may be selected from the group consisting of acrylic acid and vinyl pyrolidone. The 2-propenoic acid groups are typically present in the amount of from 0.1 to 5 moles of carboxyl groups per kilogram. The poly(2-propenal, 2-propenoic acid) polymers typically have a number average molecular weight of over 1000 and most preferably over 2000. Typically the molecular weight is less than 10,000.

The antimicrobial of the invention is a derivative of poly (2-propenal, 2-propenoic acid) prepared by reaction with an alcohol or phenol to form protected carbonyl groups. The protected carbonyl groups are formed from the 2-propenal groups which react with the alcohol to form hemiacetal and acetal groups. The alcohol is preferably a polyol by which is meant that it preferably contains at least two hydroxyl groups. Alkanols such as $C_1$ to $C_{10}$ may be used. Where the alcohol is a polyol the reaction may produce acetals or hemiacetals formed by reaction of one or more than one alcohol group.

Furthermore when two alcohol groups react it is possible for them to react at the same carbonyl or different carbonyl groups within the polymer.

Referring to the above formula I and hemiacetal and acetal forms the invention produces derivatives in which there are fewer units of formula I and forms a group wherein one or more groups R are derived from an alcohol, or when the alcohol is a polyol, more than two groups R may together form a bridging group such as a cyclic acetal group.

The propensity for polyols to give rise to internal cyclic groups will depend on the spacing and configuration of the polyol. The preferred alcohols are polyalkylene glycols and more preferred alcohols are polyethylene glycols.

The molecular weight of the polyalkylene glycols are preferably from 200 to 2000 and more preferably from 200 to 1000.

The formation of the antimicrobial of the invention from poly(2-propenal, 2-propenoic acid) may be examined by proton nuclear magnetic resonance ($^1$H.n.m.r). The poly(2-propenal, 2-propenoic acid) starting material exhibits a signal at about $\delta 5.5$ in $D_2O$ due to hydrogen bonded hydroxyl groups. This signal is significantly reduced or absent in the antimicrobial of the invention by virtue of acetal formation.

Preferably, the alcohol such as polyethylene glycol is present during the preparation of the antimicrobial polymers in an amount of between 50 and 99% by weight. Relatively dilute compositions of the acrolein polymer are particularly preferred where the alcohol is a polyol as the incidence of intermolecular cross-linking is reduced by dilution.

More preferably, polyethylene glycol is present during preparation of the polymers in the amount of between 64 and 95% by weight.

Base or alkali is preferably added to the polymers before and/or during heating, thereby enhancing the antimicrobial activity of the polymers.

Preferably, the addition of the base or alkali brings the pH of the poly(2-propenal, 2-propenoic acid) polymers to between 7 and 9. Still more preferably, the pH is about 8. The base is preferably an alkali metal hydroxide carbonate bicarbonate or mixture.

In a still further form of the invention, the release of free acrolein monomer is inhibited, from continuous release, whereby the polymers are less likely to present a source of tissue or dermal irritation.

We have found that the antimicrobial of the invention has significantly improved activity in controlling gastrointestinal disease when compared with the poly(2-propenal-2-propenoic acid) from which it is prepared. The superactivated derivative of the present invention may be used to treat a wide range of animals (including humans) and a wide range of microbial infections.

The antimicrobial of the invention may be used in treatment of gastrointestinal disease in humans, however it is particularly preferred that it be used in treatment of other animals particularly animals selected from the group consisting of dogs, pigs, sheep, horses, goats, cattle, cats, poultry, ducks, turkeys and quail.

The antimicrobial of the invention may be formulated for oral or rectal administration. Rectal administration may be particularly useful in ruminant animals. Oral formulations for ruminant animals may also be prepared using enteric coatings to provide optimal activity in the later part of the gastrointestinal tract.

The antimicrobial of the invention is particularly useful in treatment and prophylaxis of gastrointestinal ulcers, diarrhea and gastrointestinal cancers. The antimicrobial of the invention may also be used to improve the rate of weight gain in farm animals.

We have found that the antimicrobial of the invention may be used as a growth promotant in place of the presently used antibiotics. Drug resistance in pathogenic bacteria is a problem of major clinical importance in human medicine. This problem is exacerbated by the use of important antibiotics in animal feed to provide weight gain in farm animals particularly poultry and pigs. Indeed, in some European countries the use of conventional antibiotics in animal feeds has been banned. The antimicrobial of the invention may be used in treatment of animals to significantly extend the useful life of conventional antibiotics in human treatment.

We have found the antimicrobial of the invention to be effective against a wide range of microbes including protozoa, Gram positive bacteria and Gram negative bacteria. Of the Gram negative bacteria the antimicrobial of the invention has been found to provide broad spectrum activity against coliforms or Enterobacteria. It is particularly useful in treatment of gastrointestinal diseases resulting from infection by *E. coli* such as enterotoxigenic *E. coli* and β-haemolytic *E. coli*. Colibacillosis is a devastating disease in the pig-rearing industry. The disease is generally associated with proliferation of β-haemolytic *E. coli* in the small intestine after weaning and gives rise to high mortality rates and morbidity rates in young weaner piglets and as a result, failure to make normal weight gains.

Coccidiosis is a protozoal disease of animals particularly poultry and if left uncontrolled has a devastating effect. We have found that the antimicrobial of the invention may be used in the treatment or prevention of coccidiosis in birds particularly in poultry. In chickens typical clinical signs of coccidiosis include lack of thriving, rapid loss of weight, diarrhea and dysentery. The most serious effects take place in the intestine where the protozoa tend to invade the mucosa and cause epithelial damage, lesions and haemorrhage. Vaccines have been used in an attempt to prevent coccidiosis but have side effects including the tendency to reduce weight and feed efficiency.

The antimicrobial of the invention may be used in combination with other drugs known to have activity against coccidiosis. Such drugs include nitro-carbanilide, quinoline, pyridon, guanidine, quinoxaline, toltrazural, toluamide, potentiated sulfa drugs and ionophore with carbanilide.

Clostridia are Gram positive bacteria responsible for serious disease in a range of animals. For example, necrotic enteritis is a disease known to affect commercial poultry. Clostridia produce exotoxins which are some of the most toxic of all known toxins. Necrotic enteritis particularly effects broilers of between 14 and 42 days of age. The condition causes pronounced apathy, diarrhea and can cause death within hours.

Upper gastrointestinal disease including chronic gastritis, gastric ulcer and duodenal ulcer are significant human health problems. *Helicobacter pylori* is understood to be responsible for the development of ulcers and the development of gastrointestinal cancers particularly adenocarcinoma of the stomach. We have found the antimicrobial of the invention to be particularly useful against *H. pylori* in gastrointestinal disease in animals.

When the antimicrobial of the invention is incorporated into an animal feed or water this may be done in the usual manner. In a preferred embodiment the antimicrobial of the invention is incorporated in a premix. The premix will preferably include the antimicrobial, a physiologically acceptable carrier and optionally a feedstuff. The premix is generally in a relatively concentrated form and is adapted to be diluted with other material such as one or more of the other carriers, vitamins and mineral supplements and feedstuff to form the final animal feed. The premix preferably includes the antimicrobial in a concentration in the range of from 0.1 to 70% by weight, preferably 0.5 to 50% by weight. The optimum concentration will depend on whether the treatment is preventative, for control or remedial and whether the antimicrobial of the invention is the only active or whether it is used in concomitant therapy with other materials or antimicrobials.

In a preferred embodiment the concentrated composition of the antimicrobial is in a controlled-release form. The controlled release form will include the antimicrobial and a polymeric material for providing controlled release of the antimicrobial from the controlled-release system and is particularly useful in compositions for addition to solid feed material. As a result of the controlled release formulation the release of the antimicrobial may be delayed so as to occur mainly in the duodenum. A controlled release polymer may also minimize rejection of the composition due to taste or be used for rectal suppositories.

An antimicrobial composition in accordance with the invention may be in the form of pellets, pills or like solid composition. The pellets containing the antimicrobial of the invention may be prepared by the steps of:
 (i) dissolving said antimicrobial in an aqueous alkaline or basic solution;
 (ii) neutralizing said solution with acid;
 (iii) adding to said neutralised solution insoluble, cross-linked, absorbent polymers of acrylic acid and/or copolymers of acrylamide and acrylic acid, to form wet swollen pellets; and
 (iv) optionally, wholly or partially drying said wet swollen pellets.

The so-formed wet, swollen pellets may be used either wet, partially dried or wholly dried, as an additive to, for example, animal feed. This system is further designed so that the carboxyl-containing groups of the outer polymeric matrix cause the Subject Polymers to remain essentially contained within the matrix when in the acidic environment of the stomach. However, in the alkaline environment of the duodenum, the carboxyl groups of the matrix become ionised and mutually-repelling, and the pellet rapidly swells to allow the Subject Polymers, aided by repulsion among their own ionic groups, to be excluded by a diffusion process, approximately matching the speed of passage of feed through the duodenum.

In this invention, the term, "controlled release system" is used in the same context as that in, and includes the same range of examples as quoted in "Controlled Drug Delivery" (Robinson & Lee, 1987). Many other pH-sensitive controlled-release systems which are known in the art (Robinson and Lee, 1987) may be substituted for the polymer of acrylic acid or copolymer of acrylamide and acrylic acid. For example, soluble and anionic, or insoluble cross-linked and anionic, cellulosic systems; or soluble and anionic, or insoluble cross-linked and anionic polymers derived from any generic acrylic acid polymer and/or its derivatives. Such cross-linked and insoluble polymers are preferred since they swell and also are less likely to be metabolised.

It is preferred that the controlled release system comprises a pH-sensitive, cross-linked, water-absorbent pellet, which when wet is a gel.

The invention also provides an animal feed composition comprising the antimicrobial of the invention and a feedstuff. The antimicrobial is preferably present in an amount of from 0.0001 to 25% of the total feed composition and preferably from 0.0001 to 5% of the total feed composition.

In another preferred embodiment, the antimicrobial of the invention may be formulated for addition to the drinking water of animals.

The antimicrobial of the invention is preferably administered in amounts of from 0.05 to 5000 mg/kg of bodyweight/day more preferably from 0.05 to 50 mg/kg/day.

Examples of suitable inert carriers for use in compositions for administration of the antimicrobial of the invention include water, olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides, polyvinyl alcohol, partially hydrolysed polyvinyl acetate and mixtures thereof.

Solid forms for oral or rectal administration may contain pharmaceutically or veterinarally acceptable binders, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose or flavonoid glycosides such as neohesperidine dihydrochalcone. Suitable disintegrating agents include corn starch, methylcellulose, polyvinlypyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavourings. Suitable coating agents include polymers or copolymers of acrylic acid and/or methacrylic acid and/or their esters, and/or their amides, waxes, fatty alcohols, zein, shellac or gluten. Suitable preservatives include sodium benzoate, vitamin E, $\alpha$-tocopherol, ascorbic acid, methyl parabens, propyl parabens or sodium bisulphate. Suitable lubricants include magnesium stearate, stearic acid, sodium oleate, sodium chloride or talc. Suitable time delay agents include glyceryl monostearate or glyceryl distearate.

Suspensions for oral or rectal administration may further comprise dispersing agents and/or suspending agents. Suitable suspending agents include sodium carboxylmethylcellulose, methylcellulose, hydroxypropylmethylcellulose, poly-vinyl-pyrrolidone, sodium alginate or cetyl alcohol. Suitable dispersing agents include lecithin, polyoxyethylene esters or fatty acids such as stearic acid, polyoxyethylene sorbitol mono- or di-oleate, -stearate or -laurate, polyoxyethylene sorbitan mono- or di-oleate, -stearate or -laurate and the like.

The composition of the antimicrobial may further comprise one or more emulsifying agents. Suitable emulsifying agents include dispersing agents as exemplified above or natural gums such as gum acacia or gum tragacanth.

Compositions for administration in the method of the invention may be prepared by means known in the art for the preparation of compositions (such as in the art of veterinary and pharmaceutical compositions) including blending, grinding, homogenizing, suspending, dissolving, emulsifying, dispersing and where appropriate, mixing of the Subject Polymers together with selected excipients, diluents, carriers and adjuvants.

For oral administration, the pharmaceutical or veterinary composition may be in the form of tablets, lozenges, pills, troches, capsules, elixirs, powders, including lyophilised powders, solutions, granules, suspensions, emulsions, syrups and tinctures. Slow-release, or delayed-release, forms may also be prepared, for example in the form of coated particles, multi-layer tablets or microgranules.

It is generally preferred that poly(2-propenal, 2-propenoic acid) is prepared from poly(2-propenal) by oxidation of the solid in air. The poly(2-propenal) polymer may be initially heated, predominantly in the dry state, to between 80 and 110° C. More preferably, the polymer is initially heated to about 85° C. The poly(2-propenal, 2-propenoic acid) is preferably heated in the alcohol for a period in the range of from 1 hour to 1400 hours and more preferably from 1 hour to 60 hours.

In accordance with the present invention there is further provided a preservative compound or composition comprising the antimicrobial of the invention.

In accordance with the present invention there is yet still further provided a disinfectant or antiseptic compound or composition comprising the antimicrobial of the invention.

In this application the antimicrobial composition of the invention may comprise further components. An antiseptic composition of the invention may be in the form of a lotion or product for washing such as a skin cleaner, soap bar or the like. Lotions are compositions which smooth or moisturize the skin. Lotions will preferably include an emollient. Examples of emollients include polyhydric alcohols such as glycerin, sorbitol, mannitol and propylene glycol and its homopolymers; fatty acid esters of monohydric alcohols such as isopropyl palmitate, isopropyl myristate and similar esters; polyol esters of fatty acids, ethoxylated lanolins, vegetable oils, mineral oils. Such compounds will be known to formulators of cosmetics.

Compositions of the invention for use as disinfectants or antiseptics may comprise surfactants. Suitable surfactants may be anionic, non-ionic or amphoteric.

Examples of anionic surfactants useful herein include but are not limited to soaps, sulfates, sulfonates and carboxylates such as alkyl carboxylate salts, and so forth. More specifically, useful anionic surfactants include alkyl sulfates and sulfonates, alkyl ether sulfates and sulfonates, alkyl aryl sulfates and sulfonates, aryl sulfates and sulfonates, sulfated fatty acid esters, sulfonated fatty acids, sulfated monoglycerides, sulfonated olefins, primary or secondary alkane sulfonates, alkyl sulfosuccinates, acyl taurates, methyl acyl taurates, acyl isothionates, alkyl glyceryl ether sulfonate, sulfonated methyl esters, alkyl phosphates, acyl glutamates, acyl sarcosinates, alkyl sulfoacetates, acylated peptides, alkyl ether carboxylates, acyl lactylates, anionic fluorosurfactants, ethoxylated alkyl sulfates, alkyl glyceryl ether sulfonates, fatty acyl glycinates, alpha-sulfonated fatty acids, their salts and/or their esters, alkyl ethoxy carboxylates and so on and so forth, and mixtures thereof.

Any counter cation can be used in the anionic surfactant. Preferably the counter cation is selected from the group consisting of sodium, potassium, or derived from diethanolamine, or triethanolamine. More preferably the counter cation is sodium or potassium.

One particularly preferred group of anionic surfactants are selected from the group consisting of disodiumdecyl(sulfoxy)benzene sulphonate, sodium lauryl sulfate and disodium oxybis(decylsulfophenoxy)benzene sulfonate.

When the composition is in the form of a skin cleaner the composition may include a soap. A soap is a surfactant having neutral to alkaline pH typically derived by neutralization of fatty acids with alkaline compounds such as alkali metal hydroxide or alkanolamines.

Examples of non-ionic surfactants include but are not limited to alkyl polyglycosides, alcohol ethoxylates such as fatty alcohol ethoxylates and/or propoxylates, alkyl phenolethoxylates, glycol ester surfactants, PEG(20) sorbitan monooleate, polyethylene glycol cocoate, propylene oxide/ethylene oxide block polymers, alkanolamines, and so forth.

Preferred non-ionic surfactants include polyoxyalkylene glycol based surfactants. Preferred polyoxyalkylene based surfactants include hexitan esters such as polysorbates, polyethoxylated alkylphenols, poloxamers, polyethoxylated fatty alcohols, polyoxyethylene glycol monoethers, alkyl polyglucosides and ethoxylated polysiloxanes.

Examples of amphoteric surfactants useful herein include but are not limited to betaines, amine oxides, sultaines, and so forth. More specifically, examples of useful amphoteric surfactants include alkyl betaines (oleyl betaine and lauryl betaine), cocamidopropyidimethyl betaine, cocamido betaine, alkyl sultaines, alkyl amphoacetates (cocamphoacetate), alkyl amphodiacetates (cocamphodiacetate), alkyl amphopropionates, alkyl amphodipropionates (cocamphocarboxypropionate), cocamphocarboxy propionic acid, cocamidopropylhydroxysultaine, alkyldimethyl amine oxides, coconut monoethanolamine, cetydimethylamine oxide, stearamine oxide, oleamine oxide, cocamidopropylamine dimethyl oxide, and so forth.

The antiseptic or disinfectant may be in the form of an emulsion comprising an oil phase, an aqueous phase and an emulsifier. In one example the composition may comprise from 10 to 60% by weight of oil phase; 1 to 15% by weight of one or more emulsifiers; 30 to 90% by weight of aqueous phase and at least 0.001% by weight of the antimicrobial of the invention.

We have found that the polymeric antimicrobial significantly enhances the activity of a wide range of other active agents including antimicrobials for antiseptics and disinfectants and chemotherapeutics for use in gastrointestinal treatment.

We believe that the other active agents are adsorbed by the polymeric antimicrobial of the invention. The adsorption and its effect may be examined by examining membrane penetration of the further active alone and in combination with the polymeric antimicrobial across a membrane in contact with solvent.

In a further aspect the invention provides an antiseptic or disinfectant comprising an antimicrobial polymer according to the invention and a further antimicrobial or chemotherapeutic adsorbed thereon.

The antimicrobial of the invention may be used in combination with other antimicrobial substances such as those selected from the classes of EDTA, lower alkanols, phenols, isothiazolinones, glutaraldehyde, alkyl parabens and mixtures thereof. When used further antimicrobials are preferably selected from glutaraldehyde, EDTA, alkyl parabens (particularly methyl parabens) isothiazolinones and phenols.

Compositions containing phenolic antimicrobials or glutaraldehyde generally have an unpleasant odour. Fragrances and perfumes have been used to mask the odour but are not particularly effective, particularly for phenols. We have found that the antimicrobial of the invention significantly reduces the odour problem associated with the use of these compounds.

Examples of suitable phenolic compounds include halo phenols, preferably ortho- or para-substituted halo phenols such as o-chlorophenol; alkylhalo phenols such as chloroxyphenol (p-chloro-m-xylenol); alkyl phenols such as t-amylphenol; aryl phenols such as o-phenyl phenol, and benzyl-substituted halophenols such as o-chloro-p-benzylphenol. Preferably, the phenolic compound is t-amylphenol, o-chloro-p-benzylphenol, p-chloro-m-xylenol, or o-phenyl phenol. Most preferably, the phenolic compound is p-chloro-m-xylenol (PCMX).

Examples of suitable isothiazolinones include 2-alkyl-4-isothiazoline-3-ones. Preferred isothiazolinones include 2-(n-octyl-4-isothiazolin-3-one), 4,5-dichloro-2-cyclohexyl-3-isothiazolinone, 4,5-dichloro-2-(n-octyl-4-isothiazolin-3-one), 5-chloro-2-methyl-4-isothiazolin-3-one, and 2-methyl-4-isothiazolin-3-one.

When one or more further antimicrobial components are used the amount of the antimicrobial of the invention may be as described above. In the case of further antimicrobials the amounts used will depend on the type of antimicrobial. Typical amounts of the preferred additional antimicrobials are:
  (a) a phenol in an amount of 0.001 to 10%;
  (b) an isothiazolinone in an amount of 0.001 to 1%;
  (c) glutaldehyde in an amount of 0.2 to 4% and
  (d) alkanol in an amount of 20 to 99.9%.

The antimicrobial is useful with sunscreen agents such as aminobenzoates, salicylates, benzophenones, anthranilates, dibenzoylmethanes and camphor derivatives.

In accordance with a further aspect of the invention we provide a composition for treatment of gastrointestinal disease comprising an antimicrobial polymer as hereinbefore described and a further chemotherapeutic agent wherein the further chemotherapeutic agent is adsorbed onto the antimicrobial.

The adsorption will typically reduce membrane penetration of the further chemotherapeutic. The suitable chemotherapeutics for use in this embodiment are those which exhibit a significant reduction in membrane penetration when admixed with the polymeric antimicrobial. Preferably the penetration is inhibited by a factor of at least 50%.

The useful chemotherapeutic agents for use in this aspect of the invention include antibiotics for treatment of gastrointestinal disease and anticancer agents for treatment of gastrointestinal cancers.

The use of chemotherapeutics in combination with the polymeric antimicrobial reduces membrane penetration of the chemotherapeutic thereby reducing systemic side effects and providing more targeted therapy. In many cases odour is also reduced.

Examples of chemotherapeutics for treatment of gastrointestinal disease include antibiotics and anticancer agents.

Examples of antibiotics which may be used in combination with the antimicrobial polymer include tetracyclines, penicillins, aminoglycosides, sulfa drugs, cephalosporins and nitrofurans.

The antibiotics may be conventional antibiotics used to treat infections of the gastrointestinal tract.

Examples of anticancer agents which may be used in combination with the polymeric antimicrobial of the invention are alkylating agents, antimetabolites, anticancer antibiotics, plant alkaloids, hormones and other anticancer agents. Particularly anticancer agents containing carbon, hydrogen and oxygen only.

The invention has been found to significantly increase the stability of poly(2-propenal, 2-propenoic acid) polymers. Since the prior art recorded some instability of poly(2-propenal, 2-propenoic acid), as evidenced by loss of antimicrobial activity of its compositions, we conducted "accelerated ageing" at elevated temperature, ie. at 40° C. However, to our greatest surprise, the elevated temperature of "ageing" poly (2-propenal, 2-propenoic acid) in aqueous or in aqueous-polyethylene glycol solutions at 40° C., not only slowed the decrease in antimicrobial activity-but in fact, actually increased antimicrobial activity of the poly(2-propenal, 2-propenoic acid), see Example 2(a) and (b). This finding is totally contradictory and unexpected in view of the prior art which predicts that the rise in temperature should lead to "accelerated ageing", ie. accelerated loss of antimicrobial activity.

Henceforth, the process of providing increased antimicrobial activity by the formation of a new configuration of the subject polymers including poly(2-propenal, 2-propenoic acid), is referred to as "super-activation" and the polymers referred to as "super-activated polymers".

Even more surprising, in view of prior art, the inventors have found superactivation in aqueous polyethylene glycol solution is promoted by basic, followed by acidic conditions. Also, super-activation is promoted by heat and moisture.

Super-activation is facilitated by the presence of polyethylene glycols or polyols or alkanols, we believe, since the presence of the polyethylene glycol or polyol or alkanol protects and stabilizes the carbonyl groups of the polymers, by formation of acetals, from alkaline degradation by the Cannizarro reaction.

An added advantage of super-activation is that it reduces or eliminates, contaminant acrolein which is a source of tissue and dermal irritation.

It is emphasized that super-activation is quite distinct and additional to any increase of antimicrobial activity which may result, merely from more polymer being available in any aqueous test-medium as the result of increased hydrophilicity of the polymer such as was demonstrated in lapsed Australian Patent Application AU-A-11686/95 (hereinafter "11686/95"). The inventors have repeated exactly the method described in 11686/95 and then, following, found that subsequent super-activation of the partially soluble polymer demonstratively gave rise to additional, substantial antimicrobial activity. It should be noted that even super-activation did not render the polymer from 11686/95 completely soluble-in contrast to super-activation beginning with polymer firstly heated between to 80-85° C.

The optimum time to achieve super-activation of solutions of poly(2-propenal, 2-propenoic acid) depends inversely upon the temperature. It will be apparent that even ageing at room temperature may be used for superactivation, especially when facilitated in the presence of hydroxylic solvent and/or base followed by acidity, but obviously, this may be impractical due to the longer time periods required.

The inventors have found polymers super-activated as described herein, suitable for gastrointestinal therapy, preservatives in water-based products or processes, and active ingredients in disinfectants or antiseptics having the advantage of enhanced antimicrobial activity. Furthermore, the inventors found that the antimicrobial activity of such disinfectants or antiseptics was increased by increase in their pH, for example above pH 6.

A common feature of the invention is the attachment of a group capable of hydrophobic interaction, to the antimicrobial of the invention, by way of hemiacetal/acetal formation or by way of adsorption, in order to enhance antimicrobial activity.

The invention will now be described with reference to several Examples, which should not be construed as limiting the scope thereof.

Biocidal Test

Dissolve sample with 1% by weight aqueous sodium bicarbonate to obtain the required concentration (unless specified to the contrary, 0.125% by weight of polymer). Weigh 19.9 g of diluted sample into a sterile jar and inoculate with 0.1 mL of $10^7$-$10^8$ cfu of *Ps.aeruginosa* and mix. At specified time-intervals, transfer 1 mL of inoculated sample to 9 mL of Letheen broth and vortex. Plate out serial 1 in 10 dilutions. Pour with trypticase soy agar. Incubate 3 days at 37° C.

EXAMPLE 1

The example describes a method of preparing poly(2-propenal, 2-propenoic acid) by oxidation of a solid acrolein polymer in air. This poly(2-propenal, 2-propenoic acid) is the preferred method of preparing a starting material for use in the method of the invention. Water (720 mL at ambient temperature, about 20° C.) and acrolein (60 g; freshly distilled, plus hydroquinone added to 0.25% w/w) were placed in an open beaker, within a fume cupboard, and very vigorously stirred, mechanically. Then, 0.2 M aqueous sodium hydroxide (21.4 mL) was added to bring the pH 10.5-11.0.

The solution immediately turned a yellow typical of the hydroquinone anion and within a minute, the colour had disappeared and the clear solution became milky.

About 1 minute later, precipitation of a white flocculent polymer began, and appeared complete within 15-30 minutes. The precipitate was filtered and washed with water (250 mL), dried at room temperature upon filter papers for 2 days (yield 25 g), then spread as a thin layer in glass petri dishes and heated at 40° C./8 hours. This heating was continued at the following schedules : 50° C./15 hours ; 65° C./4 hours ; 75° C./18 hours ; 84° C./24 hours.

It is envisaged that this method may be scaled-up to include, eg the stepwise addition of acrolein, in a closed vessel, and followed by more rapid drying (compare example 10).

Typically, a solution of the resulting poly(2-propenal, 2-propenoic acid) was prepared by adding 2 g of the subject polymer, with stirring over 15-30 minutes, to a 1% w/w aqueous sodium carbonate solution (100 mL), and then diluted as required. Such solutions were perfectly clear-in contrast to attempted dissolutions, using alternatively, polymer derived from Example 5 of 11686/95.

EXAMPLE 2

This example describes acetal formation from poly(2-propenal, 2-propenoic acid).

(a) 5 g of poly(2-propenal, 2-propenoic acid) was dissolved in 64 g polyethylene glycol ("PEG") 200 and combined with 31 g of a 0.71% w/w solution of sodium carbonate. A portion of the solution (apparent pH=5.8) was retained at room temperature while (b) the remainder of the sample from part (a) was heated at 60° C. for periods of 12 or 25 days.

Samples from (a) and (b) were diluted with 1% w/w sodium bicarbonate and submitted for biocidal testing at polymer concentrations of 0.125% w/w. Surprisingly, the samples which had undergone "accelerated ageing" showed improved antimicrobial activity, as can be seen by reference to Table 1:

TABLE 1

| | Cfu/mL* (*Pseudomonas aeruginosa*) | | | | |
|---|---|---|---|---|---|
| Sample | 0 min | 10 min | 15 min | 30 min | 60 min |
| 25 days at room temperature | $7.8 \times 10^6$ | $4.1 \times 10^6$ | $6.1 \times 10^5$ | $9.8 \times 10^4$ | <10 |
| 12 days at 60° C. | $7.7 \times 10^6$ | $1.4 \times 10^6$ | $9.8 \times 10^3$ | <10 | <10 |

TABLE 1-continued

| | Cfu/mL* (*Pseudomonas aeruginosa*) | | | | |
|---|---|---|---|---|---|
| Sample | 0 min | 10 min | 15 min | 30 min | 60 min |
| 25 days at 60° C. | $1.0 \times 10^7$ | $1.3 \times 10^6$ | $6.6 \times 10^4$ | <10 | <10 |

*Colony forming units/mL 1 g poly(2-propenal, 2-propenoic acid) was dissolved in 200 mL of 0.1% w/w $Na_2CO_3$ and allowed to stand overnight. Sodium lauryl sulphate was introduced at a level of 0.05% w/w and the solution was acidified with HCl to pH 5.9. Portions were stored at both room temperature and 60° C. Biocidal Tests were carried out on 0.125% w/w polymer solutions, with 1% w/w $NaHCO_3$ used as the diluent. The "aged" sample showed a surprising improvement in performance, as can be seen by reference to Table 2:

TABLE 2

| | Cfu/mL* (*Pseudomonas aeruginosa*) | | | |
|---|---|---|---|---|
| Sample | 0 min | 10 min | 15 min | 30 min |
| 20 days at room temperature (RT) | $9.0 \times 10^6$ | $5.1 \times 10^5$ | $6.8 \times 10^2$ | <10 |
| 7 days at 60° C. + 13 days at RT | $9.0 \times 10^6$ | $1.2 \times 10^2$ | <10 | <10 |

*Colony forming units/mL (c) A 5% w/w solution of super-activated polymer was prepared as in example (2a) but replacing PEG200 with PEG1000. A portion of this solution was treated with conc. NaOH to pH 8.1. Samples were heated at 60° C. and submitted for biocidal testing. The sample exposed to more basic conditions, unexpectedly gave superior biocidal performance, as can be seen by reference to Table 3:

TABLE 3

| | Cfu/mL* (*Pseudomonas aeruginosa*) | | | | |
|---|---|---|---|---|---|
| Sample | 0 min | 5 min | 10 min | 15 min | 30 min |
| pH 5.8, 12 days 60° C. | $3.8 \times 10^6$ | $2.7 \times 10^6$ | $1.5 \times 10^6$ | $3.3 \times 10^3$ | <10 |
| pH 8.1, 7 days 60° C. | $90 \times 10^6$ | — | 10 | <10 | <10 |
| pH 8.1, 17 days 60° C. | $8.3 \times 10^6$ | $3.3 \times 10^5$ | $1.3 \times 10^2$ | <10 | <10 |

*Colony forming units/mL

EXAMPLE 3

This example examines the product produced by reaction of the poly(2-propenal, 2-propenoic acid) with polyethylene glycol.

The poly(2-propenal, 2-propenoic acid) of Example 1a was dissolved in a PEG 200 and 31 g of 0.71% w/w solution of sodium carbonate at pH 5.8. This composition was divided into two samples.

Sample A was retained at room temperature and examined to determine the properties of normally activated poly(2-propenal, 2-propenoic acid) in PEG 200.

Sample B was heated to 90° C. for two hours to cause the PEG and poly(2-propenal,2-propenoic acid) to react to form superactivated product.

Sample A and Sample B were examined by $^1$H Nuclear Magnetic Resonance (NMR) spectra at 600 MHZ.

The spectra of the compounds and the assignment of signals is shown in the table below.

Table of $^1$H NMR Spectra

| Normally Activated δ (ppm) | Groups | Super Activated δ (ppm) | Groups |
|---|---|---|---|
| 1.1-2.9 | —CH—, —CH$_2$— | 1.0-2. | —CH—, —CH$_2$— |
| 3.3-4.8 | —CHO—, —CH$_2$O— | 3.3-5.1 | —CHO—, —CH$_2$O— |
| 3.6 | —CH$_2$O— (PEG) | 3.6 | CH$_2$O— (PEG) |
| 4.9 | HOD | 4.9 | HOD |
| 5.1-5.5 | =CH$_2$ | 5.1-5.5 | =CH$_2$ |
| 5.5 | —OH | | |
| 5.7-6.0 | —CH= | 5.7-6.0 | —CH= |
| 9.3-9.6 | —CH=O | 9.3-9.6 | —CH=O |

The presence of the acetal adduct in the superactivated sample is shown by the absence of the signal at δ5.5 which is observed in the normally activated composition. The signal at δ5.5 in the normally activated spectrum is due to hydrogen bonded hydroxyl (—OH) groups whereas the signal is absent in the superactivated product as a result of acetal formation.

EXAMPLE 4

(a) 5% w/w solutions of polymers of a range of degrees of super-activation, apparent pH 5.7, were prepared similarly to example 2(a), but varying the percentage of PEG 200.

Samples were heated at 60° C. and stabilities were monitored over time. Physical stability was considered to have failed with the occurrence of precipitation or gelling. UV measurements were made on a 0.01% w/w polymer concentration in 1% w/w sodium carbonate solution. A decrease of the ratio of absorption at 268 nm:230 nm is considered synonymous with a decrease in chemical stability. Results are shown in Table 4:

TABLE 4

| | A | B | C | D |
|---|---|---|---|---|
| Composition | | | | |
| PEG 200 (% by weight) | 0 | 50 | 64 | 95 |
| Physical Stability Time | | | | |
| 4 days 60° C. | Fail | Pass | Pass | Pass |
| 11 days 60° C. | Fail | Fail | Pass | Pass |

TABLE 4-continued

| | A | B | C | D |
|---|---|---|---|---|
| Chemical Stability | Ratio = $\frac{\text{260–270 peak absorbance}}{\text{228–235 peak absorbance}}$ | | | |
| Time | | | | |
| 0 days 60° C. | 1.38 | 1.41 | 1.43 | 1.46 |
| 4 days 60° C. | 0.98 | 1.04 | 1.21 | 1.27 |
| 11 days 60° C. | — | 0.97 | 1.03 | 1.09 |
| 18 days 60° C. | — | 0.89 | 0.92 | 1.04 |
| 25 days 60° C. | — | — | 0.84 | 1.04 |

Both physical and UV spectral results demonstrate the positive effect of PEG on stability; higher PEG content results in greater physical and chemical stabilities.

(b) The following solutions A and B were prepared by dissolving 4 g of poly(2-propenal, 2-propenoic acid) in 196 g 1% w/w sodium bicarbonate and adjusting the pH to 7 (A) and 5.5 (B) with dilute HCl. Solution C was prepared by dissolving 50 g of poly(2-propenal, 2-propenoic acid) in PEG 200 (640 g) at 65° to –70° C. Then a solution of 4 g sodium carbonate in water (306 g) was added, the apparent pH being 7, and then 5.5 at the end of the treatment period of 31 days.

All samples were stored at 40° C. At various time intervals samples containing equivalent to 0.125% w/w polymer were submitted for biocidal testing. Results are shown in Table 5:

TABLE 5

| Time (days) at 40° C. | Time for complete kill (minutes) <10 cfu/mL (*Pseudomonas aeruginosa*) | | |
|---|---|---|---|
| | Solution A | Solution B | Solution C |
| 0 | 30 | 30 | 30 |
| 7 | 30 | 60 | — |
| 14 | — | — | 10 |
| 31 | 60 | 60 | 10 |

EXAMPLE 5

1 g of poly(2-propenal, 2-propenoic acid) was heated in either a dry or a humid, enclosed chamber, both at 60° C., for 3 days. Solutions of the dry polymer and the humidified polymer, respectively were prepared at 0.125% w/w (with correction for moisture content) and submitted for evaluation by the Biocidal Test:

TABLE 6

| | Cfu/mL* (*Pseudomonas aeruginosa*) | | | | | |
|---|---|---|---|---|---|---|
| Sample | 0 min | 5 min | 10 min | 15 min | 30 min | 60 min |
| Polymer (dry) | $4.9 \times 10^6$ | — | $7.6 \times 10^5$ | $5.9 \times 10^4$ | $1.2 \times 10^2$ | <10 |
| Polymer (humidified) | $1.1 \times 10^7$ | $6 \times 10^6$ | $3.4 \times 10^3$ | $3.7 \times 10^3$ | <10 | — |

*Colony forming units/mL

The polymers exhibited carbonyl and/or carboxyl absorption in the I.R. between 1700-1730 cm$^{-1}$, carbonyl groups (e.g. with Schiff's reagent) and have $M_w$=Ca. 10000 and $M_n$=ca.5000; titration shows carboxyl groups ca. 5 mole %. These parameters are similar (but not the same) as those of poly(2-propenal, 2-propenoic acid).

EXAMPLE 6

In duplicate experiments, a sample of polymer was prepared and then dissolved in ethane-diol, exactly as described in Example 5 of 11686/95. Half of this material was further heated at 80° C. for 24 hours (following which, solubility in aqueous media remained incomplete). The samples were compared for antimicrobial activity, using the standard Biocidal Test. Both of the samples treated by heating, ie. super-activation showed a clear enhancement of antimicrobial activity, as shown in Table 7:

TABLE 7

| Treatment | Cfu/mL* (*Pseudomonas aeruginosa*) | | | | |
|---|---|---|---|---|---|
| of solution | Initial Count | 5 min | 10 min | 15 min | 30 min |
| (1) None | 4.6 × 10$^6$ | 5.7 × 10$^5$ | 2.9 × 10$^2$ | <10 | <10 |
| (2) None | 4.6 × 10$^6$ | 4.2 × 10$^5$ | 1.5 × 10$^2$ | 10 | <10 |
| (1) 24 hours 80° C. | 4.6 × 10$^6$ | 3.7 × 10$^6$ | <10 | <10 | <10 |
| (2) 24 hours 80° C. | 4.6 × 10$^6$ | 8.0 × 10$^5$ | <10 | <10 | <10 |

*Colony forming units/mL

EXAMPLE 7

50 g of poly(2-propenal, 2-propenoic acid) was dissolved in PEG200 (640 g) at 65 to −70° C. Then, an aqueous solution of sodium carbonate (4 g) in water (306 g) was added. The sample was divided and either stood at room temperature or heated at 80° C. for 24 hours. The acrolein content of the solution was determined over time, by reverse phase HPLC and results are shown in Table 8:

TABLE 8

| Days stored | Acrolein Content (ppm) | |
|---|---|---|
| at 20° C. | Superactivated | Not Superactived |
| 0 | 274 | 144 |
| 7 | — | 126 |
| 16 | 34 | 103 |
| 30 | 13 | 80 |

EXAMPLE 8

Solutions of poly(2-propenal, 2-propenoic acid) were prepared as in Example 7 and treated at temperatures of 40, 60, 80, 100 and 115° C. for varying time periods. Samples were subjected to the standard Biocidal Test to confirm the increased kill rate and results are shown in Table 9.

TABLE 9

| Super-activation Temperature (° C.) | Optimum Time Range (Hours) | Total Kill Time (minutes) |
|---|---|---|
| Room Temperature | >1400 | <10 |
| 40 | 1400 | <10 |
| 60 | 120-170 | <10 |
| 80 | 16-24 | <10 |
| 100 | 4-7 | <10 |
| 115 | 1-3 | <10 |

The amount of time required for super-activation is seen to be inversely proportional to temperature. All solutions of polymers derived from the superactivation process were completely miscible, in all proportions, with aqueous solvents.

EXAMPLE 9

(a) 540 g of poly(2-propenal, 2-propenoic acid) was dissolved in 2304 g PEG200 at 65° C., prior to mixing with 43.2 g of sodium carbonate in 712 g of water. Then, the solution was heated to 100° C. for 4 hours, and 36 g sodium lauryl sulphate, 7 g ECOTERIC T20 (nonionic detergent) and 2 g lemon fragrance were added. The formulation, pH6, was diluted 1:30 with hard water and challenged against *Staphylococcus aureus* (a Gram-positive bacterium, of particular significance regarding infections in hospitals) and *Salmonella choleraesuis* (a Gram-negative bacterium, of particular significance regarding infections in food preparation areas), respectively using the Association of Agricultural Chemists Official Methods of Analysis (1995) 991.47, 991.48, (Hard Surface Carrier Test Method). Results are shown in Table 10:

TABLE 10

| Micro-organism | Positive Tubes | Result |
|---|---|---|
| S aureus | 2/60 | Pass |
| S. choleraesuis | 1/60 | Pass |

Adjustment of this formulation to higher pHs, increases the antimicrobial activity, as monitored by the Biocidal Test. Results are shown in Tables 11(a) and 11(b):

TABLE 11(a)

Activity against *Staphylococcus aureus*
Initial Count, 3 × 10$^6$ cfu/mL; polymer 350 ppm.

| pH | 10 minutes cfu/mL | 20 minutes cfu/mL | 30 minutes cfu/mL | 45 minutes cfu/mL | 60 minutes cfu/Ml |
|---|---|---|---|---|---|
| 5.6 | 2.9 × 10$^5$ | 4.4 × 10$^4$ | 2.3 × 10$^3$ | 20 | <10 |
| 7.2 | 2.7 × 10$^3$ | <10 | <10 | <10 | <10 |
| 8.9 | 3.2 × 10$^3$ | <10 | <10 | <10 | <10 |
| 10.5 | 1.1 × 10$^2$ | <10 | <10 | <10 | <10 |

TABLE 11(b)

Activity against *Pseudomonas aeruginosa*
Initial Count, 3.7 × 10$^6$ cfu/mL; polymer 350 ppm.

| pH | 10 minutes cfu/mL | 20 minutes cfu/mL | 30 minutes cfu/mL | 45 minutes cfu/mL | 60 minutes cfu/mL |
|---|---|---|---|---|---|
| 5.6 | 2.9 × 10$^5$ | 8.6 × 10$^4$ | 6.2 × 10$^2$ | 40 | <10 |
| 7.2 | 5.8 × 10$^5$ | 9.1 × 10$^4$ | 4.3 × 10$^3$ | <10 | <10 |
| 8.9 | 9.5 × 10$^5$ | 8.2 × 10$^4$ | 4.6 × 10$^2$ | <10 | <10 |
| 10.5 | 1.1 × 10$^2$ | 3.0 × 10$^3$ | <10 | <10 | <10 |

(b) 1200 g of poly(2-propenal, 2-propenoic acid) was dissolved in 7680 g of PEG200 at 60° C. and then 96 g $Na_2CO_3$ in 3024 g water was added. The solution was heated at 100° C. for 6 hours.

The formulation was added to the basin of an induced draft cooling tower, to a concentration of 300 ppm (30 ppm polymer) 3 times/week. Dosing was carried out at evening to allow contact times of 8-12 hours before operation recommenced; residual concentration was expected to be halved every 3-6 hours of operation. Recirculation water had on average, temperature 27° C., pH 8.5, conductivity 3000 µS. Microbial counts were determined and compared to an adjacent, identical, tower which was dosed with a biodispersant, daily. Results are shown in Table 12:

TABLE 12

| Treatment Time | Cfu/mL* | |
| --- | --- | --- |
| (days) | Treated Tower | Control Tower |
| 1 | $2.4 \times 10^3$ | $1.1 \times 10^7$ |
| 2 | $2.0 \times 10^3$ | $1 \times 10^6$ |
| 3 | $3.3 \times 10^3$ | — |
| 4 | $2.5 \times 10^3$ | — |
| 14 | $6.1 \times 10^4$ | $2.6 \times 10^6$ |
| 15 | $5.1 \times 10^4$ | $1.1 \times 10^6$ |
| 16 | $5.1 \times 10^4$ | $4.9 \times 10^6$ |

*Colony forming units/mL

The data indicate the treatment programme maintained the microbial counts within the guidelines of AS/NZ Standard 3666.3 (Int):1998 and below that in the adjacent tower, containing biodispersant (which was found to be unusually inadequate during the demanding conditions of the very hot, summer period of the test).

EXAMPLE 10

10(a) Comparative Example

This example demonstrates a method of preparing an acrolein polymer in which the method of the invention is not used.

1.0 0.8% w/w Sodium Hydroxide

Place 9.90 kg of deionised water in a 10L stainless steel vat and add 0.08 kg sodium hydroxide to the water and stir until dissolved.

2.0 Polymerisation

Place 100.1 kg of deionised water in a 200 L stainless steel vat and add 4.99 kg of the 0.8% w/w sodium hydroxide solution to the 200 L vat. Equilibrate the solution to 15-20° C. Simultaneously add 20 kg acrolein monomer and the remaining 0.8% w/w sodium hydroxide solution to the 200 L vat at a rate over 1 hour such that the pH remains at 10.5-11.0, and the temperature does not rise above 30° C. Continue the polymerisation for a further 90 minutes.

3.0 Washing

Filter/centrifuge the polymerisation mixture and wash the polymer with deionised water until the pH of the wash water is less than 7.0. The approximate yield is 8 kg.

4.0 Drying

Dry the polymer in air, then heat in an oven using the following program.

| Step | Time | Temperature |
| --- | --- | --- |
| 1 | 2 hrs | 25° C. |
| 2 | 1 hr | 40° C. |
| 3 | 1 hr | 70° C. |
| 4 | 1 hr | 75° C. |
| 5 | 2 hrs | 85° C. |

5.0 Dissolution

Place 400L of water in a 500 L vat and add 4 kg of sodium carbonate and stir until dissolved. Slowly add 8 kg of dry, heated polymer and stir for thirty minutes.

The resulting polymer was found to have an approximate solubility of 90-95% w/w in 1% w/w sodium carbonate.

EXAMPLE 10(b)

This example describes a method of preparing an acrolein polymer in which the polymer of comparative example is super activated by the method of the invention.

1.0 Base Manufacture

Dissolve 0.4 kg sodium carbonate in 30.6 kg water in a suitable container and place 64 kg polyethylene glycol 200 into the mixing vessel. Commence stirring with the mechanical stirrer and heat the glycol PEG200 to 65±3° C. Add 5 kg of the dry acrolein polymer from Example 10a to the glycol and stir until a uniform mixture is obtained.

NOTE: The solid may not completely dissolve at this stage. Slowly add the sodium carbonate solution to the glycol mixture at a rate that ensures the pH of the solution remains in the range 3.5-9.0.

NOTE: The solution foams copiously so care must be taken not to allow it to overflow.

Stir the solution for 45 minutes at 65±3° C.

NOTE: pH should be within the range 7-9. Temperature should be within the range 65±3° C.

2.0 Superactivation

Cover the mixing vessel and heat to 100° C. for four (4) hours. The resulting polymer was found to have an approximate solubility 99.5-100% w/w in water.

EXAMPLE 11

This example examines the antimicrobial activity of the dry, normally activated poly(2-propenal, 2-propenoic acid) polymer of Example 10a and the antimicrobial activity of the superactivated acetal derivative described in Example 10b.

Chickens treated each of the antimicrobials were compared with a control group according to the following procedure:

In each trial 20 Cob chickens (Line 53), day old were purchased from a commercial hatchery. They were weighed, sexed and randomly assigned into adjacent pens in a room of an isolated animal house. There was an even distribution of male and female chickens. Water and feed were available ad libitum. The diet was a commercial crumble (Chick Starter, Milne Feeds: 18% crude protein) with a coccidiostat present (125 ppm Dinitolomide).

Ten chickens were administered the formulation of 0.1% w/w of normally activated antimicrobial from Example 10a in the water for 14 days through static drinkers; dose rate of 30 mg/kg/day. The other ten chickens were the Control Group.

Both groups of chickens were weighed on days 0, 4, 7, 11 and 14. At the completion of the trial all chickens were euthanised, and the treated chickens were autopsied post mortem. A thorough gross examination of the thoracic and abdominal cavities was performed.

Results:

TABLE 13a

Weight gained during trial with normally activated antimicrobial of Example 10a

| Day | Control Group (Average Weight in g) | Treatment Group (Average Weight in g) | Differences between groups (%) |
| --- | --- | --- | --- |
| 0 | 42.5 | 42.5 | 0 |
| 4 | 65.0 | 72.5 | 11.5 |
| 7 | 98.5 | 98.0 | −0.5 |
| 11 | 145.5 | 148.5 | 2.4 |
| 14 | 185.5 | 200.5 | 8.1 |

The treatment group had measurably greater weight gains at the end of the 14-day period in comparison to the control group.

At the completion of the trial, at post-mortem, no clinical or pathological signs of toxicity were evident at this gross examination in the treated group of chickens.

TABLE 13b

Weight gains during trial with superactivated acetal antimicrobial of Example 10b

| Day | Control Group (Average Weight in g) | Treatment Group (Average Weight in g) | Differences between groups (%) |
| --- | --- | --- | --- |
| 0 | 42.5 | 42.5 | 0 |
| 4 | 62.5 | 67.5 | 8 |
| 7 | 97.5 | 103 | 6 |
| 11 | 130 | 145 | 11.5 |
| 14 | 178 | 219 | 23 |

At post mortem at the completion of the trial, on the remaining chickens, no clinical or pathological signs were evident at gross examination in both groups.

Conclusion:

There was a significant difference in weight gains in the treatment group in comparison to the control group ($x^2$; P<0.015). The treatment group was 23% heavier than the control group at the completion of the trial.

The significant improvement in weight gain of the super-activated acetal derivative relative to the control, and in the next example, when compared with the normally activated poly(2-propenal, 2-propenoic acid) demonstrates the significant improvement in enteric antimicrobial activity of the acetal derivative.

EXAMPLE 12

This example demonstrates the enteric antimicrobial activity of the acetal derivative of poly(2-propenal, 2-propenoic acid) prepared according to the procedure of Example 10b.

Material and Methods:

Sixteen weaner pigs (age: 18 days ±2 days and weight: 5.5 kg ±1.0 kg) were purchased from a commercial piggery. They were randomly assigned into 2 groups of 8 pigs (equal distribution of sexes) and housed in an environmentally controlled isolation animal house.

Water and feed were available ad libitum upon entry to the animal house, and the diet was a commercial antimicrobial-free weaner pellet [19% crude protein].

All the weaner pigs were euthanised with an intravenous injection of sodium barbiturate, and then necropsied. DNA from Gastric and Oesophageal regions of the stomach of twenty-four weaner pigs were extracted at necropsy using a Qiagen Dneasy tissue kit according to provided instructions. 3 µL of the extracted DNA was used to test for the presence of *Helicobacter* spp. in the biopsy tissue samples. Polymerase Chain Reaction (PCR) was conducted twice on each sample with seven control DNA samples being included in each PCR run. No discrepancies were found between the PCRs conducted.

Results:

Coding of Treatments:

Group 1: No treatment (negative control).

Group 2: 0.1% w/v of superactivated polymeric antimicrobial according to Example 10b; 30 mg/kg/day.

TABLE 14

PCR results of *Helicobacter spp.* using previously optimized genus specific primers where + represents a positive detection of *Helicobacter spp.* and − represents no detection.

| Group Number | Gastric Region | Oesophageal Region |
| --- | --- | --- |
| 1 | − | − |
| 1 | − | + |
| 1 | − | + |
| 1 | − | + |
| 1 | + | − |
| 1 | − | − |
| 1 | + | + |
| 1 | − | − |
| 1 | − | + |
| 2 | − | − |
| 2 | − | − |
| 2 | − | − |
| 2 | − | − |
| 2 | − | − |
| 2 | − | − |
| 2 | − | − |
| 2 | − | − |

In group 1 (no treatment) there were five positive PCR results to *Helicobacter* spp (1—Gastric, 4—Oesophageal), while in group 2 (0.1% w/v of polymeric antimicrobial) there were no positive PCR results.

Conclusion:

The acetal derivative of poly(2-propenal, 2-propenoic acid) at 0.1% w/v significantly ($x^2$: P<0.025) reduces the incidence of porcine *Helicobacter* spp in the gastric and oesophageal mucosa in weaner pigs.

EXAMPLE 13

This example evaluates the polymeric antimicrobial of Example 10b under field conditions for the control of porcine post weaning colibacillosis (PWC).

Method:

146 Young pigs [weaners], either receiving various formulations of superactivated antimicrobial in their feed or water, APRALAN® (Elanco) orally, autogenous vaccination, or neither, were challenged with the stresses associated with weaning on a large commercial piggery that had a long history of problems with PWC.

Their responses in the development of diarrhea, weight gains, and mortality were assessed and are recorded in Table 15.

TABLE 15

|  | Superactivated polymeric antimicrobial group number | Mortality Rates [% died][2] | Diarrhoea days [Days loose: score 1-2][3] | Mean Faecal Score[4] |
|---|---|---|---|---|
| Superactivated polymeric antimicrobial | 1 | 3.33 [F;P < 0.0001] | 1.79 [F;P < 0.0001] | 0.14 [F;P < 0.0001] |
|  | 2 | 0 [F;P < 0.0001] | 1.17 [F;P < 0.0001] | 0.11 [F;P < 0.0001] |
| Untreated control group | 3 | 16.67 [F;P < 0.05] | 3.77 [F;P < 0.0001] | 0.41 [F;P < 0.0001] |
| Apralan ® group | 4 | 13.33 [F;P < 0.05] | 3.89 [F;P < 0.0001] | 0.38 [F;P < 0.0001] |
| Vaccinated Group | 5 | 6.67 [F;P < 0.0001] | 3.10 [F;P < 0.0001] | 0.30 [F;P < 0.0001] |

Notes:
1. Coding of treatments:
i. Group 1 = 0.1% w/w superactivated polymeric antimicrobial in feed
ii. Group 2 = 0.02% w/v superactivated polymeric antimicrobial in water
2. Percentage of group that died from PWC during the trial
3. The mean number of days for each pig in the group when a faecal score of 1 or 2 was recorded; faecal score is a measure of the intensity of diarrhoea.
4. The sum of the faecal scores divided by the number of observed samples per pig.
5. F = Fisher's Exact Test.

Conclusion:

This field trial highlighted the following points that positively reflected on the efficacy of the acetal derivative of poly(2-propenal, 2-propenoic acid) (superactivated antimicrobial) for use in piglets in commercial piggery, when challenged with β-haemolytic *Escherichia coli* after weaning:

1. Mortality:
   Lower mortality rates for either groups treated with superactivated polymeric antimicrobial than either the untreated, vaccinated or Apralan® groups.
2. Diarrhea days:
   Significantly lower diarrhea days in either of the superactivated antimicrobial treated groups [F; P<0.0001] than in either of the untreated, vaccinated or Apralan® groups.
3. Faecal scores:
   Significantly lower mean faecal scores in either of the superactivated antimicrobial treated groups [F; P<0.0001] than in either of the untreated, vaccinated or Apralan® groups.

EXAMPLE 14

This example examines the effect of using certain additives with the antimicrobial of the invention.

Method:

Overnight broths of challenge cultures were prepared and the Total Viable Count (TVC) of the overnight cultures was estimated.

The samples were serially diluted 1 to 1 using sterile normal saline (5 mL). Sterile Hard Water (SHW) was used as diluent when testing samples containing EDTA.

1 part of each overnight culture was diluted in 9 parts diluent. The resulting diluted suspensions were used as the inocula.

Inoculate each sample dilution with 100 µL of the diluted overnight culture. (One culture per tube). Mix well.

The tubes were incubated for ≦24 hours at 37° C. (*A. niger* was incubated at 28° C. for ≦24 hours).

From each test tube, 1 mL was subcultured into 9 mL of recovery broth and mixed well (Recovery Broths: Nutrient Broth+3% Tween 80 (NBT) for polymeric antimicrobial and EDTA; Nutrient Broth+3% Tween 80+(NBTA) for glutaraldehyde and, Letheen Broth (LB) for methyl parabens).

The samples incubated at 37° C. for a further ≦48 hours. (28° C. for ≦5 days for *A niger*).

Each tube was examined for growth. All tubes were then subcultured onto selective agar and incubated for ≦24 hours at 37° C. (28° C. for ≦5 days for *A. niger*). Growth on selective agar was taken to confirm growth of the test organism.

Positive controls were performed using 5 mL of diluent inoculated with culture and subject to incubation, recovery and confirmation.

Negative controls were performed using un-inoculated 5 mL of diluent and subject to incubation, recovery and confirmation.

TABLE 16

RESULTS: Results are tabulated below
MKC of Selected Preservatives and Synergy Index

| Culture | Inoculum (cfu/mL) | 1 | 2 | 3 | 4 | 5 | 6 | 7 | 8 | 9 | 10 | 11 |
|---|---|---|---|---|---|---|---|---|---|---|---|---|
| A. niger | $3.3 \times 10^7$ | | 2000 | >250 | | 1000:125 | | | | | | |
| | $3.0 \times 10^7$ | | | | | | 2000 | >1000 | 1000:500 | | | |
| | $2.2 \times 10^7$ | | | | | | | | | 2000 | 10000 | 500:2500 |
| C. albicans | $3.0 \times 10^6$ | | 1000 | 125 | | 250:31 | | | | | | |
| | $3.2 \times 10^6$ | | | | | | 1000 | 1000 | 250:125 | | | |
| | $1.1 \times 10^7$ | | | | | | | | | 500 | 1250 | 125:62.5 |
| E. coli | $1.6 \times 10^9$ | 62.5 | | 3.5 | 3.5 | | | | | | | |
| | $1.0 \times 10^9$ | | | | | | 125 | >1000 | 62.5:31 | | | |
| | $9.6 \times 10^8$ | | | | | | | | | 62.5 | 2500 | 62.5:310 |
| P. aeruginosa | $1.9 \times 10^9$ | 250 | | 31 | 31 | | | | | | | |
| | $9.4 \times 10^8$ | | | | | | 250 | 1000 | 125:62.5 | | | |
| | $1.8 \times 10^9$ | | | | | | | | | 250 | 1250 | 62.5:310 |
| S. aureus | $1.5 \times 10^9$ | 31 | | 7 | 3.5 | | | | | | | |
| | $1.3 \times 10^9$ | | | | | | 31 | >1000 | 31:15 | | | |
| | $1.3 \times 10^9$ | | | | | | | | | 31 | 2500 | 31:150 |

Note:
all ratio values are expressed as ratio of polymeric antimicrobial:preservative Legend:
1) Polymeric antimicrobial 0.025% w/w
2) Polymeric antimicrobial 0.2% w/w
3) Glutaraldehyde 0.025% w/w
4) Polymeric antimicrobial 0.025% w/w+Glutaraldehyde 0.025% w/w
5) Polymeric antimicrobial 0.2% w/w+Glutaraldehyde 0.025% w/w
6) Polymeric antimicrobial 0.2% w/w
7) EDTA 0.1% w/w
8) Polymeric antimicrobial 0.2% w/w+EDTA 0.1% w/w
9) Polymeric antimicrobial 0.2% w/w (in 80% w/w glycerol)
10) Methyl Paraben 1% w/w (in 80% w/w glycerol)
11) Polymeric antimicrobial 0.2% w/w (in 80% w/w glycerol)+Methyl Paraben 1% w/w (in 80% w/w glycerol).

TABLE 17

Synergy Index with polymeric antimicrobial

| Culture | Glutaraldehyde | EDTA | Methyl paraben |
|---|---|---|---|
| A. niger | <0.6 | <0.5 | 0.2 |
| C. albicans | 0.3 | 0.1 | 0.5 |
| E. coli | 0.5 | <0.3 | 0.3 |
| P. aeruginosa | 0.6 | 0.4 | 0.2 |
| S. aureus | 0.3 | <0.7 | 0.2 |

Note:
Synergy < 1.0, Additive = 1.0, Antagonistic > 1.0
A = MKC polymeric antimicrobial
B = MKC Preservative
C = MKC Mix
D = Ratio of A to B
E = Ratio of B to A Conclusion:

It was shown that the acetal derivative of poly(2-propenal, 2-propenoic acid) was synergistic with Glutaraldehyde, EDTA, and Methyl Paraben, respectively versus A. niger, C. albicans, E. coli, P. aeruginosa, S. aureus.

EXAMPLE 15

This example demonstrates the activity of the antimicrobial of the invention in combination with "Dettol" brand antimicrobial.

The sample was serially diluted 1 to 1 using sterile normal saline (5 mL).

Each sample dilution was inoculated with 100 µL of the diluted overnight culture. (One culture per tube). The samples were mixed well.

They were incubated at 37±2° C. for ≦24 hours. (Aspergillus niger inoculated tubes were incubated at 28±2° C. for ≦24 hours).

From each test tube 1 mL was subcultured into 9 mL recovery broth and vortexed well (NBT or Sabouraud+Tween 80 (SABT) or A. niger).

They were incubated at 37±2° C. for ≦48 hours. (A. niger, was incubated at 28±2° C. for a further 5 days).

The recovery broths were examined for turbidity (Growth) and streaked onto selective agars to confirm growth.

TABLE 18

MKC Results in ppm of superactivated polymeric antimicrobial and/or "Dettol"

| Culture | Inoculum Approx (cfu/mL) | Polymeric Antimicrobial MKC range (ppm) | 1 | 2 | 3 | 4 | 5 |
|---|---|---|---|---|---|---|---|
| A. niger | $4.1 \times 10^7$ | 2000-500 | N/A | 1000 | 300 | N/A | 125:150 |
| C. albicans | $5.2 \times 10^6$ | 100-250 | N/A | 500 | 75 | N/A | 62.5:75 |

TABLE 18-continued

MKC Results in ppm of superactivated polymeric antimicrobial and/or "Dettol"

| Culture | Inoculum Approx (cfu/mL) | Polymeric Antimicrobial MKC range (ppm) | 1 | 2 | 3 | 4 | 5 |
|---|---|---|---|---|---|---|---|
| E. coli | $7.6 \times 10^8$ | 125-31 | N/A | N/A | 75 | 31:75 | N/A |
| P. aeruginosa | $1.8 \times 10^9$ | 250-62.5 | N/A | 250 | 600 | N/A | 125:150 |
| S. aureus | $2.0 \times 10^9$ | 31-7 | N/A | 15 | 75 | N/A | 15:19 |

Legend
1) 0.1% w/w polymeric antimicrobial
2) 0.2% w/w polymeric antimicrobial
3) "Dettol" 4.8% w/v (Diluted 1:20)
4) 0.1% w/w polymeric antimicrobial + "Dettol" (Diluted 1:20)
5) 0.2% w/w polymeric antimicrobial + "Dettol" (Diluted 1:20)

TABLE 19

Synergy Index of polymeric antimicrobial and Dettol

| Culture | Synergy Index (SI) |
|---|---|
| A. niger | 0.3 |
| C. albicans | 0.6 |
| E. coli | 0.6 |
| P. aeruginosa | 0.4 |
| S. aureus | 0.6 |

Note:
Antagonistic if SI < 1, Additive if SI = 1, Synergistic if SI < 1
SI = CD/A + CE/B
A = MKC polymeric antimicrobial (ppm)
B = MKC Dettol (ppm)
C = MKC of polymeric antimicrobial/"Dettol" Mix (ppm)
D = Ratio of polymeric antimicrobial in relation to Dettol
E = Ratio of "Dettol" in relation to polymeric antimicrobial
Note:
The active antimicrobial in "Dettol" is chloroxylenol Conclusion:

It was shown that the polymeric antimicrobial of the invention was synergistic with "Dettol" against E. coli, S. aureus, P. aeruginosa, C. albicans and A. niger. This shows that "Dettol" and the polymeric antimicrobial when used together as a mixed solution, will work substantially better than when used on their own.

EXAMPLE 16

Determination of the Effect of Superactivated poly(2-propenal, 2-propenoic acid) on Phenol Permeability

EXAMPLE

Sample A: o-Phenylphenol (OPP) (1 g) was dissolved with stirring in PEG-200 (12.8 g). Na$_2$CO$_3$ (0.08 g) and water (7.2 g) were then added and the mixture stirred until a clear solution resulted.

Sample B: o-Phenylphenol (1 g) was added to 5% Superactivated Poly(2-propenal, 2-propenoic acid) in 1:2 PEG 200/0.4% Na$_2$CO$_{3(aq)}$ (20 g).

In a special apparatus the samples were applied to one side of a 0.45 micron nylon membrane in contact with, on the other side, a stirred solution of ethanol. After 45 min the UV/Vis spectrum of the ethanol was compared with that of o-phenylphenol (max=247 nm).

TABLE 20

| Sample | max = 247 nm in ethanol before | max = 247 nm in ethanol after |
|---|---|---|
| A | no | yes |
| B | no | no |

Determination of the Effect of Superactivated poly(2-propenal, 2-propenoic acid) on Phenol Volatility Sample A had a medium odour of the o-phenylphenol but Sample B had little or no odour of the o-phenylphenol.

EXAMPLE 17

Microbiological Activity of poly(2-propenal, 2-propenoic acid) [Superactivated] on *Helicobacter Pylori*

The biocidal activity (killing efficiency) of poly(2-propenal, 2-propenoic acid) [superactivated] against *Helicobacter pylori* was determined by using a modified biocidal method.

The basis of the test was to challenge a large population of *H. pylori* culture to a specific concentration of poly(2-propenal, 2-propenoic acid) [superactivated] (0.125% w/w solution) and then estimate the surviving population over time. Due to the fastidious nature of the culture, the testing time points were defined at 0, 5, 10, 15 and 20 minutes.

Poly(2-propenal, 2-propenoic acid) [superactivated] was inoculated with *H. pylori* and sub-sampled at the specified time intervals into recovery broth. The recovery broth was then serially diluted and aliquots of the dilutions were spread-plated onto selective agars and incubated microaerophilically at 37±2° C. for 5 to 7 days.

*H. pylori* dies when exposed to air for lengthy periods. Therefore, a negative control showing the natural death rate of the culture was determined by inoculating *H. pylori* into a sterile normal saline and sub-sampling at specified time points. Plates were also incubated at microaerophilic conditions at 37±2° C. for 5 to 7 days.

Following incubation, the colony forming units were counted and averaged to determine the natural death rate, and the population decline after exposure to the superactivated antimicrobial. Preliminary results showed that at pH 7 and for the length of the test (20 minutes), there was no substantial decline in the natural die off rate of *H. pylori*. A 0.125% w/w solution of superactivated poly(2-propenal, 2-propenoic acid) [superactivated] at pH 7, gave a 1-log reduction in population after 5 minutes and total death within 10 to 15 minutes.

EXAMPLE 18

Antiseptic Qualities of poly(2-propenal, 2-propenoic acid) [Superactivated]

The antimicrobial, poly(2-propenal, 2-propenoic acid) [superactivated], was trailed for antiseptic qualities.

The number of bacteria present on the hands of subjects was determined before and after application of antimicrobial followed by donning of surgical gloves. The antiseptic effect of poly(2-propenal, 2-propenoic acid) [superactivated] was compared to the commonly used surgical antiseptic, 4% Chlorhexidine Surgical Scrub (manufactured by Orion Laboratories, in Perth, Western Australia).

- 3% w/w aqueous solutions of poly(2-propenal, 2-propenoic acid) [superactivated] reduced baseline counts of bacterial populations on gloved hands after 3 hours.
- 2% w/w aqueous solution of poly(2-propenal, 2-propenoic acid) [superactivated] with 70% ethanol showed a sustained reduction in baseline bacterial counts after 3 hours on gloved hands, as did 4% chlorhexidine.
- 3.2% w/w aqueous solution of poly(2-propenal, 2-propenoic acid) [superactivated] with 3.1% sodium lauryl sulphate, followed by 4% w/w aqueous solution of poly(2-propenal, 2-propenoic acid) [superactivated] in 70% ethanol, applied to hands prior to donning surgical gloves, gave a significant reduction in the baseline bacterial counts after 3 hours.

The results indicate that poly(2-propenal, 2-propenoic acid) [superactivated] possesses good residual antimicrobial activity that is required for sustained control of bacterial numbers in surgical asepsis. The inclusion of 70% ethanol to the formulation aids the initial rapid decrease in bacterial numbers.

The invention claimed is:

1. A method for treating gastrointestinal disease in an animal subject comprising:
   preparing a polymeric antimicrobial by reacting poly(2-propenal, 2-propenoic acid) with polyalkylene glycol in the presence of water at a temperature between 60° C. and 150° C. for between 1 to 170 hours, wherein the poly(2-propenal, 2-propenoic acid) contains from 0.1 to 5 moles of carboxyl groups per kilogram of polymer, whereby antimicrobial activity of the polymeric antimicrobial derived from poly(2-propenal, 2-propenoic acid) is increased compared with the poly(2-propenal, 2-propenoic acid); and
   administering the prepared polymeric antimicrobial to an animal subject to treat gastrointestinal disease of the animal subject.

2. A method according to claim 1 wherein the polyalkylene glycol comprises a polyethylene glycol.

3. A method according to claim 1 wherein the polyalkylene glycol is a polyethylene glycol of molecular weight in the range of from 200 to 1000.

4. A method according to claim 1 wherein the polymeric antimicrobial is present in a composition that further comprises a pharmaceutically or veterinarially acceptable inert carrier for gastrointestinal administration to animals.

5. A method according to claim 4 wherein the carrier for gastrointestinal administration is selected from the group consisting of controlled release polymers, olive oil, peanut oil, sesame oil, sunflower oil, arachis oil, coconut oil, liquid paraffin, ethylene glycol, propylene glycol, polyethylene glycol, ethanol, propanol, isopropanol, glycerol, fatty alcohols, triglycerides, polyvinyl alcohol, partially hydrolyzed polyvinylacetate and mixtures thereof.

6. A method according to claim 4 wherein the composition is in the form of a feed additive or drinking water additive comprising from 0.1 to 70% by weight of the polymeric antimicrobial.

7. A method according to claim 1 wherein the polymeric antimicrobial is administered in the form of a composition comprising an antimicrobially effective amount of the polymeric antimicrobial diluted with water.

8. A method according to claim 1 wherein the polymeric antimicrobial is administered as a drinking water composition containing in the range of from 0.0001 to 10% by weight of the polymeric antimicrobial.

9. A method according to claim 1 comprising a further administering a chemotherapeutic agent.

10. A method according to claim 1 comprising a further administering an antimicrobial.

11. A method according to claim 1 wherein the polymeric antimicrobial is orally administered.

12. A method according to claim 1 wherein the animal is suffering from at least one gastrointestinal disease selected from the group consisting of gastroenteritis, ulcer, diarrhea, dysentery, and insufficient weight gain.

13. A method according to claim 1 wherein the animal is suffering from at least one of diarrhea, gastroenteritis, and dysentery.

14. A method according to claim 1 wherein the animal is selected from the group consisting of dogs, pigs, sheep, horses, cattle, cats, poultry, ducks, turkeys and quail.

15. A method according to claim 1 wherein the animal is selected from ruminant animals and the antimicrobial is rectally administered.

16. A method according to claim 1 wherein the animal is selected from poultry and pigs.

17. A method according to claim 1 wherein the animal is a partially grown pig.

18. A method according to claim 1 used for treatment or prophylaxis of porcine post weaning coliobacillosis wherein said administering comprises orally administering an antimicrobially effective amount of the polymeric antimicrobial to young pigs after weaning.

19. A method according to claim 1 wherein the polymeric antimicrobial is administered at a dose of from 0.05 to 5000 mg/kg/day.

20. A method according to claim 1 wherein the polymeric antimicrobial is administrated at a dose in the range of from 0.5 to 500 mg/kg/day.

21. A method according to claim 18 wherein the young pigs are administered a dose of the polymeric antimicrobial in the range of from 0.05 to 50 mg/kg/day.

22. A method according to claim 1 wherein the gastrointestinal disease results from one or more microbes selected from the group consisting of Coliforms, *Salmonella*, *P.aeruginosa*, *Helicobacter*, Proteus, Enterobacteria, Yeasts, Protozoa, Clostridia and *Shigella*.

23. A method according to claim 1 wherein the gastrointestinal disease results from one or more of *H. Pylori* and Coccidia.

24. A method according to claim 1 wherein the gastrointestinal disease results from at least one of enterotoxigenic *E. coli* and β-haemolytic *E. coli*.

25. A method according to claim 1 used in treatment or prevention of necrotic enteritis in poultry comprising administering to poultry an antimicrobially effective amount of the polymeric antimicrobial.

26. A method according to claim 1 used in treatment or prevention of coccidiosis in poultry comprising administering to poultry an antimicrobially effective amount of the polymeric antimicrobial.

27. A method according to claim 1 wherein the polymeric antimicrobial is administered in an animal feed composition comprising a feed material and an antimicrobially effective amount of the polymeric antimicrobial.

28. A method according to claim 27 wherein the polymeric antimicrobial is present in an amount of from 0.001 to 25% by weight of the total feed composition.

* * * * *

UNITED STATES PATENT AND TRADEMARK OFFICE
CERTIFICATE OF CORRECTION

PATENT NO. : 7,629,002 B2 Page 1 of 1
APPLICATION NO. : 10/053088
DATED : December 8, 2009
INVENTOR(S) : Melrose et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 538 days.

Signed and Sealed this

Second Day of November, 2010

David J. Kappos
*Director of the United States Patent and Trademark Office*